(12) United States Patent
McDaniel et al.

(10) Patent No.: US 10,814,100 B2
(45) Date of Patent: Oct. 27, 2020

(54) DEFLECTABLE CATHETER WITH HINGE

(71) Applicant: BIOSENSE WEBSTER, INC., Irvine, CA (US)

(72) Inventors: Benjamin D. McDaniel, Irvine, CA (US); Martin F. O'Sullivan, Long Beach, CA (US); James K. Lee, Santa Clara, CA (US)

(73) Assignee: Biosense Webster, Inc., Irvine, CA (US)

( * ) Notice: Subject to any disclaimer, the term of this patent is extended or adjusted under 35 U.S.C. 154(b) by 71 days.

(21) Appl. No.: 16/252,528

(22) Filed: Jan. 18, 2019

(65) Prior Publication Data

US 2019/0151616 A1    May 23, 2019

Related U.S. Application Data

(63) Continuation of application No. 15/582,394, filed on Apr. 28, 2017, now Pat. No. 10,183,150, which is a
(Continued)

(51) Int. Cl.
*A61M 25/01* (2006.01)
*A61B 5/042* (2006.01)
(Continued)

(52) U.S. Cl.
CPC ......... *A61M 25/0147* (2013.01); *A61B 5/042* (2013.01); *A61B 5/6852* (2013.01); *A61B 18/1492* (2013.01); *A61M 25/005* (2013.01); *A61M 25/0136* (2013.01); *A61M 25/0138* (2013.01); *A61B 2018/00011* (2013.01);
(Continued)

(58) Field of Classification Search
CPC ............ A61M 25/0147; A61M 25/005; A61M 25/0136; A61M 25/0138; A61M 2025/015; A61M 2210/125; A61B 5/042; A61B 5/6852; A61B 18/1492;
(Continued)

(56) References Cited

U.S. PATENT DOCUMENTS 3,109,461 A    11/1963   Wolff et al.
4,353,358 A    10/1982   Emerson
(Continued)

FOREIGN PATENT DOCUMENTS

EP    0937481 A1    8/1999

OTHER PUBLICATIONS

European Search Report dated Jul. 5, 2004 in corresponding EP Application No. 04251137.8, 3 pgs.

*Primary Examiner* — Aaron F Roane
(74) *Attorney, Agent, or Firm* — Lewis Roca Rothgerber Christie LLP

(57) ABSTRACT

A deflectable device, such as a catheter, is provided that includes a hinge that enhances the ability of the device to deflect or bend within a predetermined plane. The catheter comprises an elongated tubular catheter body having proximal and distal ends and at least one lumen extending therethrough. A distal segment is provided distal to the distal end of the catheter body. A tubular hinge is provided between the distal end of the catheter body and the proximal end of the distal segment. The hinge has an axis and at least one lumen extending therethrough. The tube includes at least one slot, and preferably a plurality of slots, extending part of the way through the hinge generally transverse to the axis of the hinge.

20 Claims, 9 Drawing Sheets

Related U.S. Application Data continuation of application No. 14/320,124, filed on Jun. 30, 2014, now Pat. No. 9,636,482, which is a continuation of application No. 11/866,352, filed on Oct. 2, 2007, now Pat. No. 8,764,743, which is a continuation of application No. 10/386,868, filed on Mar. 12, 2003, now Pat. No. 7,276,062.

(51) Int. Cl.
  *A61B 18/14* (2006.01)
  *A61B 5/00* (2006.01)
  *A61M 25/00* (2006.01)
  *A61B 18/00* (2006.01)

(52) U.S. Cl.
  CPC ........... *A61B 2018/00351* (2013.01); *A61B 2018/00577* (2013.01); *A61B 2018/00821* (2013.01); *A61B 2018/1407* (2013.01); *A61M 2025/015* (2013.01); *A61M 2210/125* (2013.01)

(58) Field of Classification Search
  CPC .......... A61B 2018/00011; A61B 2018/00351; A61B 2018/00577; A61B 2018/00821
  USPC .......................................................... 606/41
  See application file for complete search history.

(56) References Cited

U.S. PATENT DOCUMENTS

| | | |
|---|---|---|
| 4,742,817 A | 5/1988 | Kawashima et al. |
| 4,911,148 A | 3/1990 | Sosnowski et al. |
| 5,273,535 A | 12/1993 | Edwards et al. |
| RE34,502 E | 1/1994 | Webster, Jr. |
| 5,304,131 A | 4/1994 | Paskar |
| 5,315,996 A | 5/1994 | Lundquist |
| 5,381,782 A | 1/1995 | DeLaRama et al. |
| 5,383,852 A | 1/1995 | Stevens-Wright |
| 5,391,147 A | 2/1995 | Imran et al. |
| 5,437,288 A | 8/1995 | Schwartz et al. |
| 5,467,763 A | 11/1995 | McMahon et al. |
| 5,581,782 A | 12/1996 | DeLaRama |
| 5,843,152 A | 12/1998 | Tu et al. |
| 5,849,011 A | 12/1998 | Jones et al. |
| 5,891,088 A | 4/1999 | Thompson et al. |
| 5,897,529 A | 4/1999 | Ponzi |
| 5,919,199 A | 7/1999 | Mers Kelly et al. |
| 5,935,102 A | 8/1999 | Bowden et al. |
| 5,961,513 A | 10/1999 | Swanson et al. |
| 5,971,975 A | 10/1999 | Mills et al. |
| 6,012,494 A | 1/2000 | Balazs |
| 6,027,863 A | 2/2000 | Donadio, III |
| 6,102,886 A | 8/2000 | Lundquist et al. |
| 6,123,699 A | 9/2000 | Webster, Jr. |
| 6,146,381 A | 11/000 | Bowe et al. |
| 6,171,277 B1 | 1/2001 | Ponzi |
| 6,183,463 B1 | 2/2001 | Webster, Jr. |
| 6,198,974 B1 | 3/2001 | Webster, Jr. |
| 6,210,409 B1 | 4/2001 | Ellman et al. |
| 6,292,695 B1 | 9/2001 | Webster, Jr. et al. |
| 6,332,881 B1 | 12/2001 | Carner et al. |
| 6,338,725 B1 | 1/2002 | Hermann et al. |
| 6,371,955 B1 | 4/2002 | Fuimaono et al. |
| 6,485,455 B1 | 11/2002 | Thompson et al. |
| 6,491,626 B1 | 12/2002 | Stone et al. |
| 6,522,930 B1 | 2/2003 | Schaer et al. |
| 6,585,717 B1 | 7/2003 | Wittenberger et al. |
| 6,585,718 B2 | 7/2003 | Hayzelden et al. |
| 6,591,472 B1 | 7/2003 | Noone et al. |
| 6,628,976 B1 | 9/2003 | Fuimaono et al. |
| 6,647,281 B2 | 11/2003 | Morency |
| 6,699,241 B2 | 3/2004 | Rappaport et al. |
| 6,733,499 B2 | 5/2004 | Scheib |
| 6,795,721 B2 | 9/2004 | Coleman et al. |
| 6,817,999 B2 | 11/2004 | Berube et al. |
| 6,866,662 B2 | 3/2005 | Fuimaono et al. |
| 6,893,436 B2 | 5/2005 | Woodard et al. |
| 7,008,375 B2 | 3/2006 | Weisel |
| 7,099,717 B2 | 8/2006 | Woodard et al. |
| 9,636,482 B2 | 5/2017 | McDaniel et al. |
| 2002/0120253 A1 | 8/2002 | Ouchi |
| 2003/0009208 A1 | 1/2003 | Snyder et al. |

DEFLECTABLE CATHETER WITH HINGE

CROSS-REFERENCE TO RELATED APPLICATION(S)

This application is a continuation of and claims priority to and the benefit of U.S. application Ser. No. 15/582,394 filed Apr. 28, 2017, now U.S. Pat. No. 10,183,150, which is a continuation of and claims priority to and the benefit of U.S. application Ser. No. 14/320,124 filed Jun. 30, 2014, now U.S. Pat. No. 9,636,482, which is a continuation of and claims priority to and the benefit of U.S. application Ser. No. 11/866,352, filed Oct. 2, 2007, now U.S. Pat. No. 8,764,743, which is a continuation of and claims priority to and the benefit of U.S. application Ser. No. 10/386,868, filed Mar. 12, 2003, now U.S. Pat. No. 7,276,062, the entire contents of all of which are incorporated herein by reference.

FIELD ON THE INVENTION

The present invention relates to an improved catheter having a hinge to enhance the ability of the catheter to bend in a desired direction.

BACKGROUND OF THE INVENTION

Deflectable catheters are widely used for a variety of applications. In the area of electrophysiology, it is often desirable to introduce a portion of a catheter carrying one or more electrodes into a certain region of the heart in order to map or ablate that region. However, due to their inherent flexibility, catheters can be difficult to control as precisely as would be desired. Accordingly, a need exists for a deflectable catheter having a mechanism to enhance the user's ability to control the degree and direction of deflection of the catheter.

SUMMARY OF THE INVENTION

The present invention provides deflectable devices, such as catheters, that include a hinge that enhances the ability of the device to deflect or bend within a predetermined plane. In one embodiment, the invention is directed to a deflectable device comprising an elongated tubing having proximal and distal ends, an axis, at least one lumen extending therethrough and a distal region at or near the distal end of the deflectable device. The tubing, which can be a single tubing or a plurality of connected tubing segments, includes at least one slot extending part of the way through the tubing in the distal region. The at least one slot is generally transverse, and preferably generally perpendicular, to the axis of the tubing. The device further includes means for deflecting the distal region of the tubing in a plane that passes through the at least one slot.

In another embodiment, the invention is directed to a deflectable device having proximal and distal ends. The device comprises a proximal region near the proximal end of the device and a distal region near the distal end of the device. A hinge is provided between the proximal and distal regions. The hinge comprises a tubing having an axis and at least one lumen extending therethrough. The tubing includes at least one slot extending part of the way through the tubing.

In yet another embodiment, the invention is directed to a deflectable catheter. The catheter comprises an elongated tubular catheter body having proximal and distal ends and at least one lumen extending therethrough. A distal segment is provided distal to the distal end of the catheter body. A tubular hinge is provided between the distal end of the catheter body and the proximal end of the distal segment. The hinge has an axis and at least one lumen extending therethrough. The hinge includes at least one slot extending part of the way through the hinge generally transverse to the axis of the hinge.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

The invention is directed to a deflectable device, such as a catheter, including a hinge that enhances the ability of the device to deflect or bend within a predetermined plane. In accordance with the invention, the device can be deflected or bent upon application of a pulling force from within the device, such as by the use of a puller wire as is generally known in the art, or the device can be bent upon application of an outside force on a part of the device, such as by pushing a part of the device again tissue to cause the tissue to thereby exert a force onto a part of the device and bend that part of the device relative to the rest of the device. As used herein, the term "deflectable" describes catheters having a straight configuration in the neutral position that can be deflected into a curved configuration, as well as catheters having a curved configuration in the neutral position that can be deflected into a straight configuration or into a different curved configuration.

Figure 1:
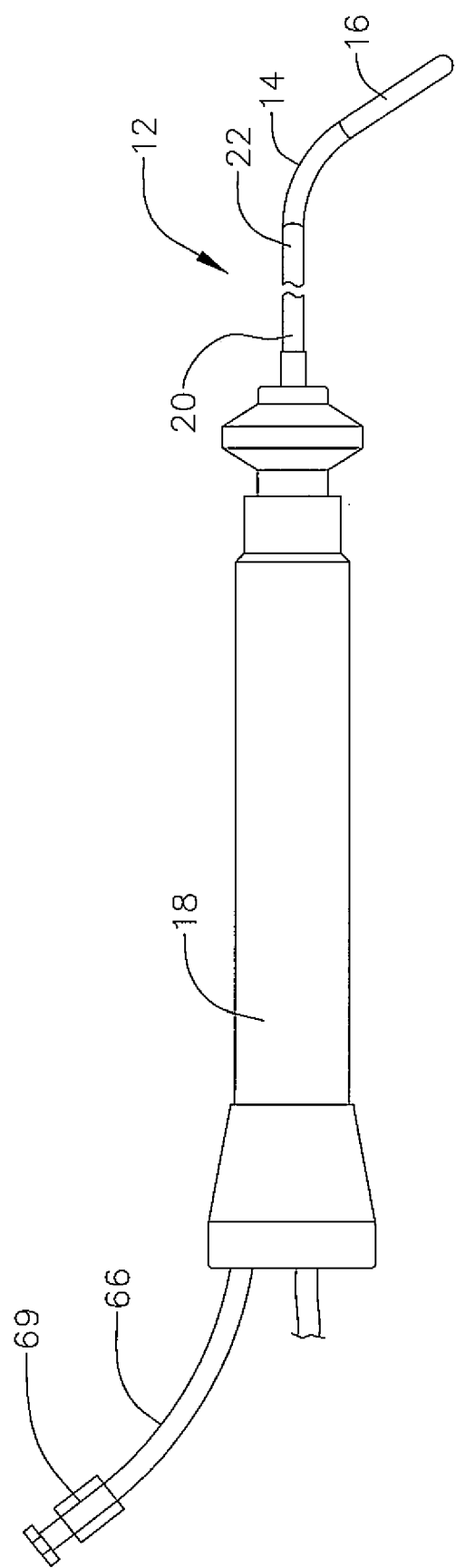
FIG. 1 is a side view of an embodiment of the catheter of the invention.

In one embodiment of the invention, there is provided a steerable catheter having an irrigated electrode at its distal end. As shown in FIG. 1, the catheter comprises an elongated catheter shaft 12 having proximal and distal ends, an intermediate shaft 14 at the distal end of the catheter shaft over which the hinge is mounted, a distal shaft 16 at the distal end of the intermediate shaft on which one or more electrodes or other devices are mounted for performing mapping, ablation or another desired function, and a control handle 18 at the proximal end of the catheter shaft.

In the depicted embodiment, the catheter shaft 12 has a proximal region 20 and a distal region 22 having different degrees of flexibility. Such a design is particularly useful where it is desired to deflect the distal region 22 of the catheter shaft. Typically the proximal region 20 is substantially longer than the distal region 22, with the proximal region having an exemplary length ranging from about 90 cm to about 120 cm, and the distal region having an exemplary length ranging from about 1 cm to about 8 cm.

Figure 2:
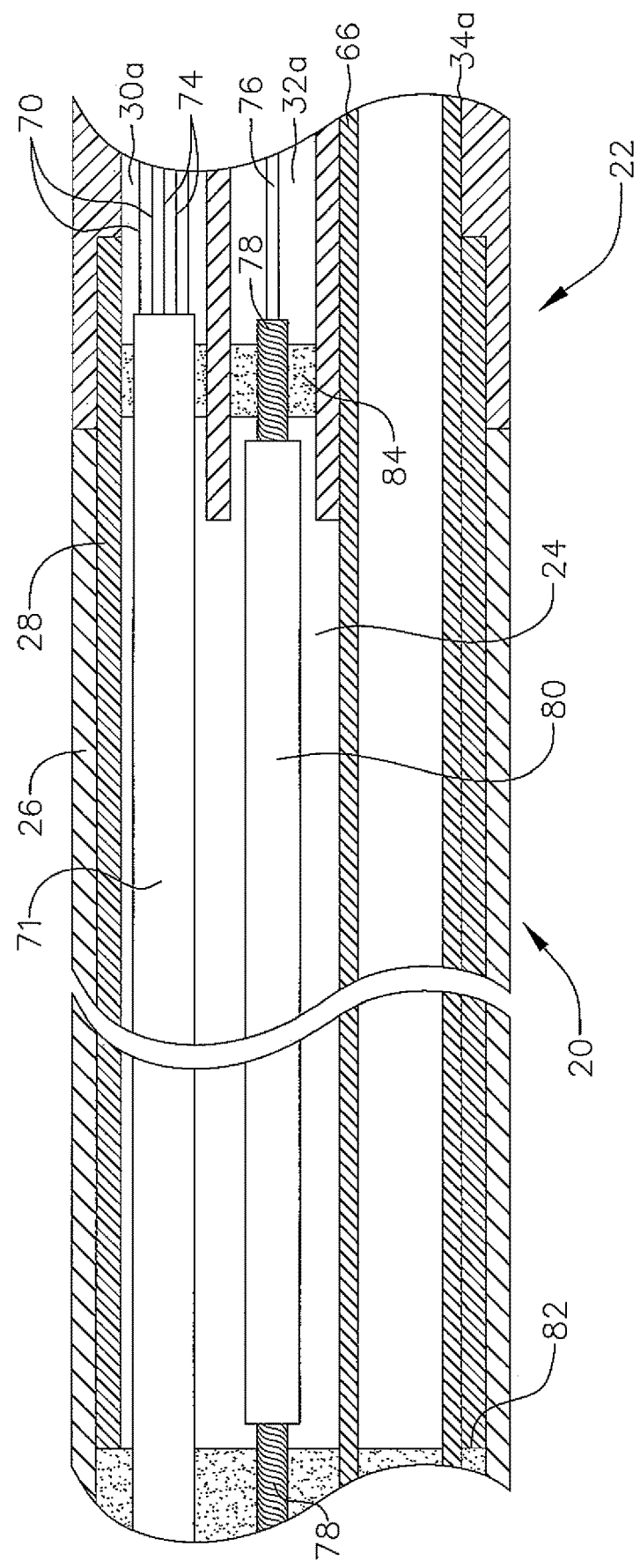
FIG. 2 is a side cross-sectional view of a catheter body according to the invention, including the junction between the proximal and distal regions of the catheter shaft of the catheter shown in FIG. 1.

With reference to FIG. 2, the proximal region 20 of the catheter shaft 12 comprises an elongated tubular construction having a single, axial or central lumen 24. The proximal region 20 is flexible, i.e., bendable, but substantially non-compressible along its length. The proximal region 20 can be of any suitable construction and made of any suitable material. A presently preferred construction comprises an outer wall 26 made of polyurethane or PEBAX. The outer wall 26 comprises an imbedded braided mesh of stainless steel or the like to increase torsional stiffness of the proximal region 20 so that, when the control handle 18 is rotated, the distal region 22 of the catheter shaft 12 will rotate in a corresponding manner.

Additionally, in the depicted embodiment, the inner surface of the outer wall 26 of the proximal region 20 is lined with a stiffening tube 28, which can be made of any suitable material, preferably polyimide. The stiffening tube 28, along with the braided outer wall 26, provides improved torsional stability while at the same time minimizing the wall thickness of the catheter, thus maximizing the diameter of the central lumen 24. The outer diameter of the stiffening tube 28 is about the same as or slightly smaller than the inner diameter of the outer wall 26.

The outer diameter of the catheter shaft 12 is not critical, but is preferably no more than about 8 french, more preferably 7 french. Likewise the thickness of the outer wall 26 is not critical, but is thin enough so that the central lumen 24 can accommodate an infusion tube, a puller wire, lead wires, and any other wires, cables or tubes.

The distal region 22 of the catheter shaft 12 comprises a short section of tubing having three lumens. The first lumen 30a electrode carries lead wires, the second lumen 32a carries a puller wire, and the third lumen 34a carries an infusion tube, as described in more detail below. The tubing of the distal region 22 is made of a suitable non-toxic material that is preferably more flexible than the proximal region 20. A presently preferred material for the distal region 22 is braided polyurethane, i.e., polyurethane with an embedded mesh of braided stainless steel or the like. The number and sizes of the lumens are not critical and will depend on the components to be carried by the lumens.

As noted above, the proximal region 20 and distal region 22 have different degrees of flexibility to enhance deflection of the distal region of the catheter shaft. However, if deflection of the distal region is less important, the catheter shaft can have a single stiffness along its length. With such a design, the proximal and distal regions can be made, for example, of a single piece of tubing having only a single lumen extending therethrough. Other catheter shaft arrangements will be apparent to one skilled in the art and are within the scope of the invention.

Figure 3:
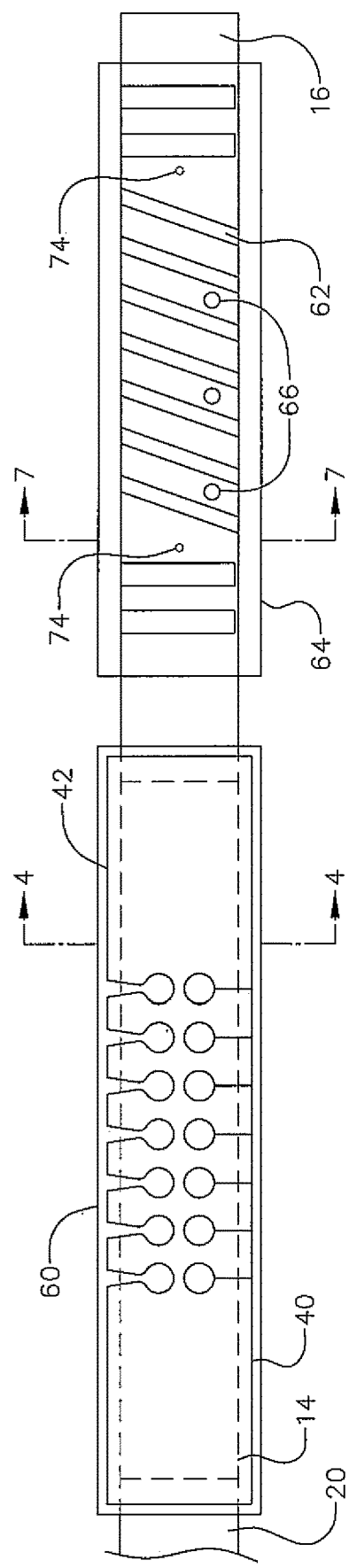
FIG. 3 is a side view of the intermediate and distal shafts of the catheter shown in FIG. 1.

At the distal end of the distal region 22 of the catheter shaft 12 is the intermediate shaft 14, which carries the hinge, and the distal shaft 16, which carries one or more electrodes or other diagnostic or treatment devices. Specifically, as best shown in FIG. 3, the intermediate shaft 14 comprises a flexible plastic tubing, preferably PEBAX. The distal shaft 16 similarly comprises a flexible plastic tubing, preferably PEBAX. The intermediate shaft 14 is more flexible than either of the distal region 22 of the catheter shaft 12 or the distal shaft 16 so as to not limit the ability of the intermediate shaft to bend, thereby allowing the hinge to control the extent and direction of bending of the intermediate shaft, as discussed further below. Unlike the tubing that forms the catheter shaft 12, the plastic tubing that forms the intermediate shaft 14 preferably does not include a braided core within the plastic. In one exemplary embodiment, the proximal region 20 comprises 72D durometer plastic, the distal region 22 comprises 55D durometer plastic, the intermediate shaft 14 comprises 35D durometer plastic, and the distal shaft 16 comprises 72D durometer plastic. The intermediate shaft 14 is connected to the distal end of the distal region 22 of the catheter shaft 12 and to the proximal end of the distal shaft 16 by any suitable method, for example, using thermal butt joints.

In the depicted embodiment, the intermediate shaft 14 includes first, second and third lumens 30b, 32b, and 34b that are aligned with the first, second and third lumens 30a, 32a, and 34a, respectively, in the distal region 22 of the catheter shaft 12. Similarly, the distal shaft 16 includes first, second and third lumens 30c, 32c, and 34c that are aligned with the first, second and third lumens 30b, 32b, and 34b, respectively, of the intermediate shaft 14. As would be recognized by one skilled in the art, the number and arrangement of lumens in the intermediate shaft 14 can vary, but the lumens in the intermediate shaft are preferably aligned with the lumens in the distal region 22 of the catheter shaft 12 and in the distal shaft 16, as discussed further below.

Figure 4:
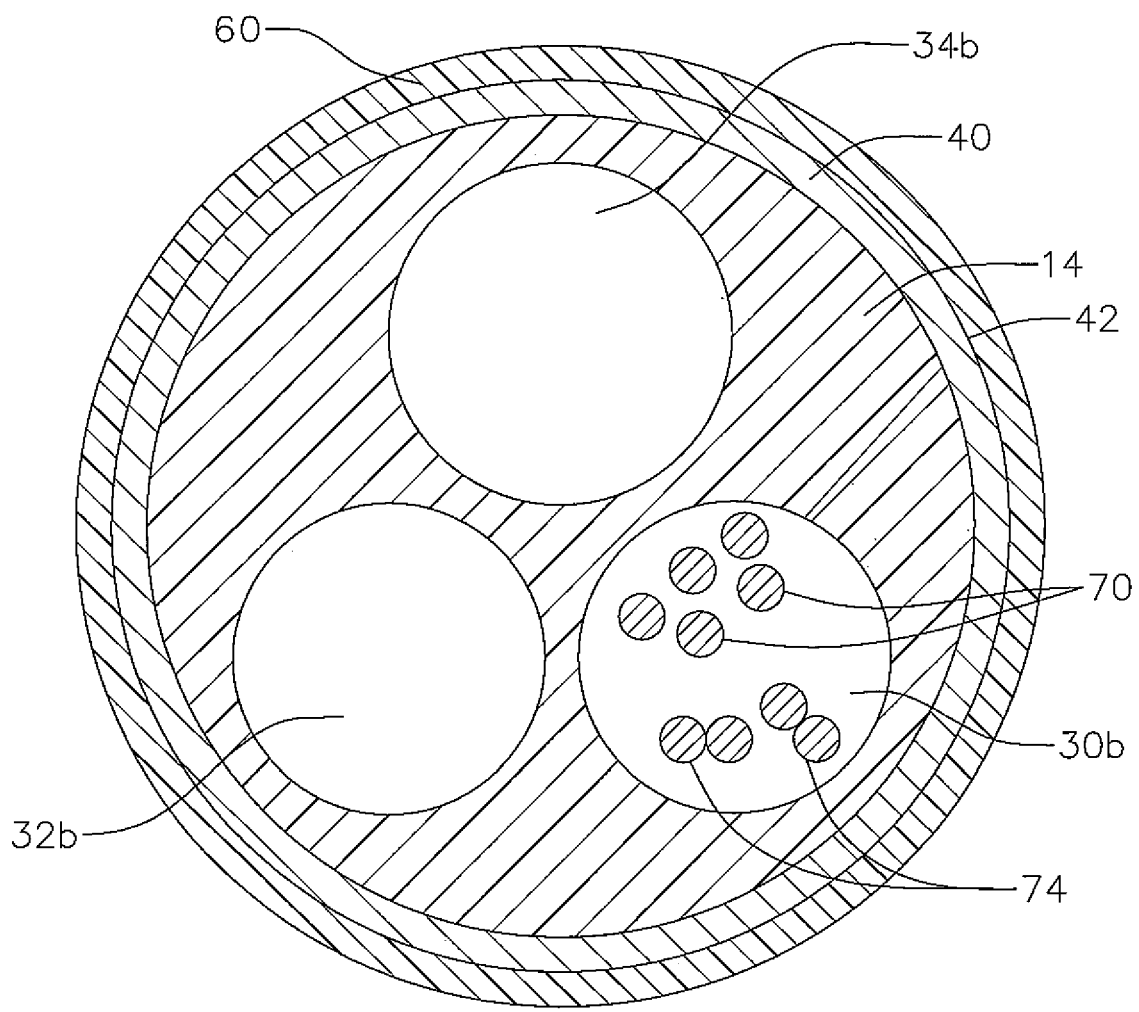
FIG. 4 is an end cross-sectional view of the intermediate shaft shown in FIG. 3.

A hinge 40 is mounted over the intermediate shaft 14 to control the direction and extent of bending of the intermediate shaft. The hinge 40 comprises a flexible tube, which can be made of any suitable material, such as Nitinol or plastic, having an outer wall 42 and an inner diameter that is slightly larger than the outer diameter of the intermediate shaft 14 so that the hinge can be mounted on the outside of the intermediate shaft, as shown in FIGS. 3 and 4. In the depicted embodiment, the hinge 40 covers the entire intermediate shaft 14 to reduce the tendency of the intermediate shaft to kink when the hinge is bent. The hinge 40 includes one or more slots 44 extending through the outer wall 42 of the flexible tube, which affect the direction in which and extent to which the hinge can bend.

Figure 5:
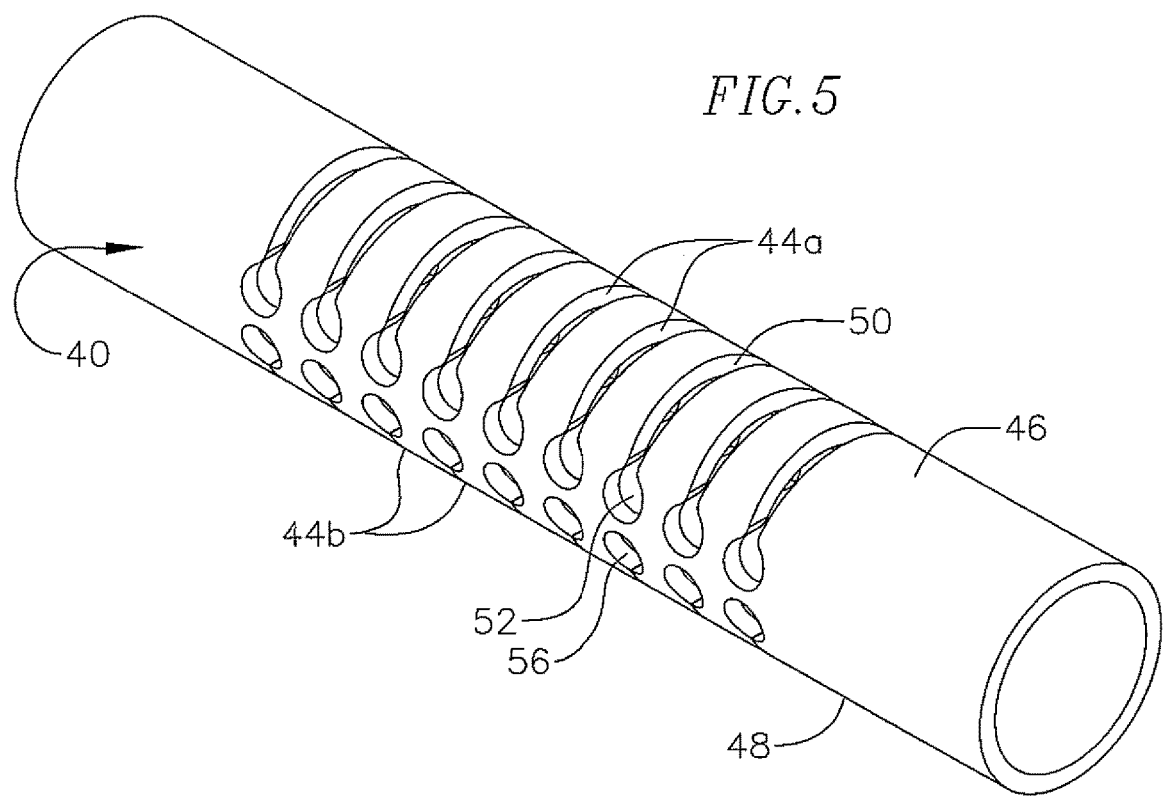
FIG. 5 is a perspective view of a hinge according to the invention in a neutral configuration.
Figure 6:
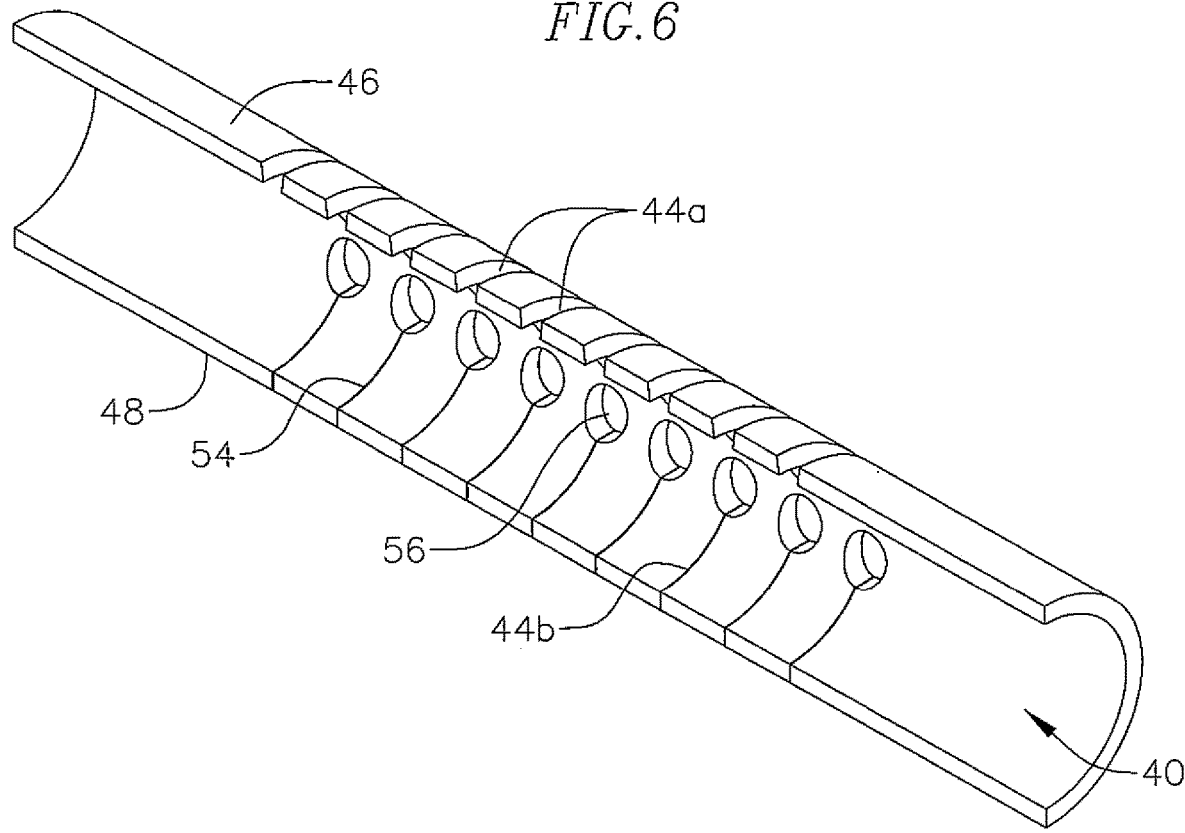
FIG. 6 is a perspective cutaway view of the hinge depicted in FIG. 5.
Figure 7:
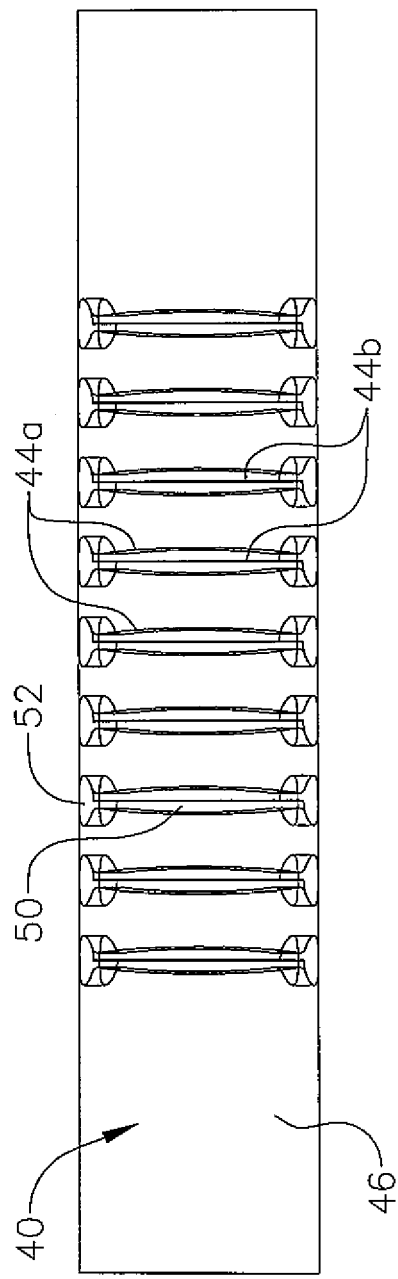
FIG. 7 is a top view of the hinge depicted in FIG. 5.

In the depicted embodiment, the slots 44 of the hinge 40 are arranged to permit the hinge to bend in a single plane in a single direction and no more than approximately 90°. With reference to FIGS. 5 and 6, the outer wall 42 of the hinge 40 has a compressible side 46 and an expandable side 48. The compressible side 46 is the side facing the direction toward which the hinge 40 bends, where the bending results in the compressible side of the hinge being compressed on itself. The expandable side 48 is the side opposite the compressible side 46.

The depicted hinge 40 includes a total of fourteen slots 44 divided evenly between the compressible side 46 and the expandable side 48. When the hinge is in the neutral position, which in the depicted embodiment is straight, as shown in FIGS. 5 to 8, each slot 44 is generally perpendicular to the axis of the hinge 40, although the slots could alternatively be angled relative to the axis of the hinge so long as they are generally transverse to the axis of the hinge. The slots 44 on the compressible side 46 ("the compressible slots 44*a*") are aligned with the slots 44 on the expandable side 48 ("the expandable slots 44*b*"), i.e., arranged so that corresponding slots on the compressible side and on the expandable side are positioned the same distance from an end of the hinge. As will become apparent, the number, placement, size and shape of the slots 44 can vary depending on the desired effect to be achieved. Preferably the total number of slots on the hinge ranges from one to about thirty, more preferably from about ten to about twenty. The slots 44 can be provided only on the compressible side 46, only on the expandable side 48 or divided in any desired manner between the two sides.

In the depicted embodiment, the slots 44 are all the same depth Q, i.e., they all extend the same distance through the outer wall 42 of the hinge 40 towards the axis of the hinge. The depicted slots do not extend through the axis or center of the hinge 40, so that the depth of each slot is less than the outer radius of the hinge. If desired, the slots can be deeper than the outer radius of the hinge so that they extend through the axis of the hinge 40, although with such a design it is preferred that the compressible slots 44*a* not be aligned with the expandable slots 44*b*, but instead alternate in position. If desired, the compressible slots 44*a* can have depths different from those of the expandable slots 44*b*. In another alternative, the compressible slots 44*a* of a single hinge can have varying depths and/or the expandable slots 44*b* can have varying depths.

Figure 8:
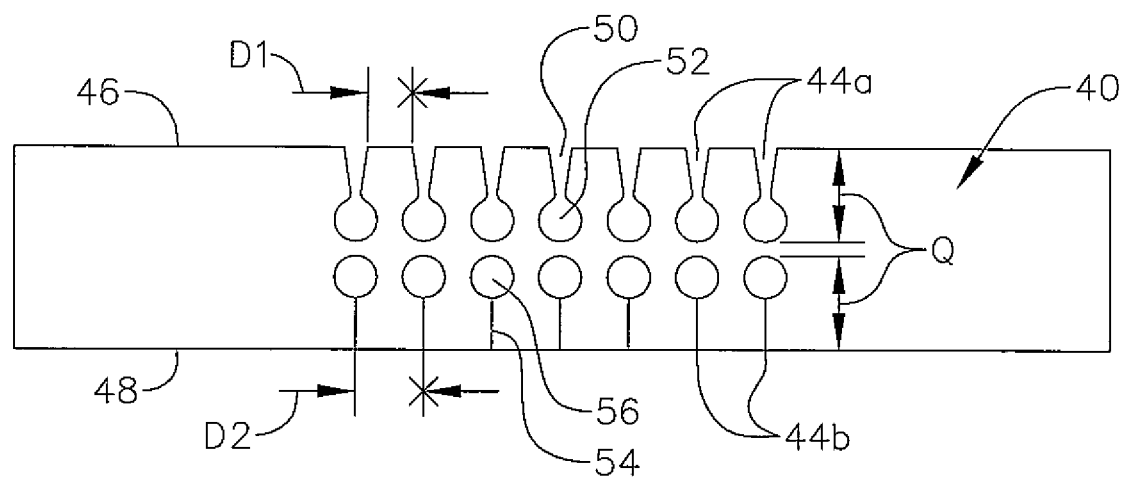
FIG. 8 is a side view of the hinge depicted in FIG. 5.

The shapes of the slots 44 can affect the extent to which the hinge 40 will bend. In the depicted embodiment, the compressible slots 44*a* are generally keyhole-shaped when viewed from the side, as best shown in FIG. 8. Specifically, each compressible slot 44*a* comprises an elongated opening 50 having two ends of decreasing width and that terminate in circular openings 52, which are preferably larger in diameter than the widest portion of the elongated opening. Thus, the compressible slots 44*a* involve the removal of material from the flexible tube that forms the hinge. In one embodiment, each elongated opening 50 decreases in width at an angle of 13°, varying from a maximum width of 0.011 inch to an end width (near the circular openings 52) of 0.006 inch, with the circular opening having a diameter of 0.020 inch, and with the distance D1 between the compressible slots 44*a* being approximately 0.021 inch.

Each expandable slot 44*b* comprises an elongated slot 54 of insignificant thickness, i.e., where no material is removed from the flexible tube, that terminates in a circular opening 56 like the circular openings 52 of the compressible slots 44*a*. In one embodiment, the circular openings 56 of the expandable slots 44*b* have the same size as the circular openings 52 of the compressible slots 44*a*, with the distance D2 between the expandable slots 44*b* being approximately 0.032 inch, so that the expandable slots 44*b* are aligned with the compressible slots 44*a*.

Figure 9:
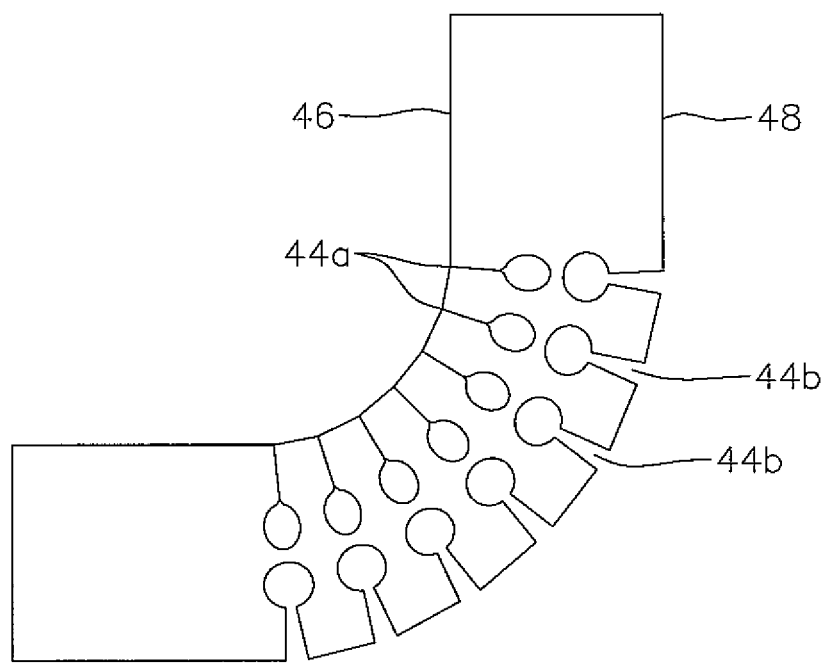
FIG. 9 is a side view of the hinge depicted in FIGS. 5 to 8 in a deflected configuration.
Figure 10:
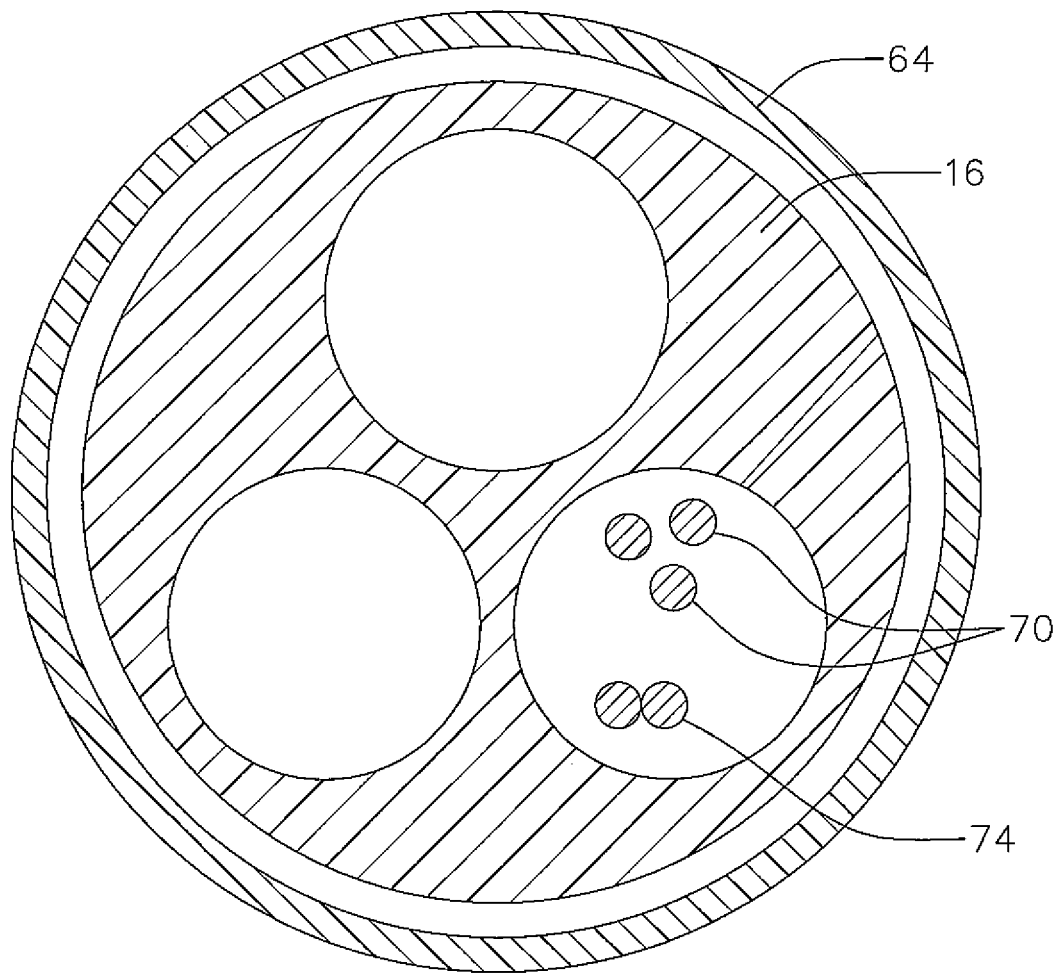
FIG. 10 is an end cross-sectional view of the distal shaft shown in FIG. 3.

In use, when a force is exerted on the distal shaft 16, which is mounted on the distal end of the hinge 40, the hinge is bent in a direction toward the compressible side 46, as shown in FIG. 9. The arrangement of the slots 44 forces the hinge to bend within the desired plane. As the hinge 40 bends, the compressible slots 44*a* are compressed so that the inwardly-angled openings 50 close, and the expandable slots 44*b* expand so that the elongated slots 54 of insignificant thickness open, as best depicted in FIG. 9. The inwardly-angled openings 50 are sized as described above such that they close and make further bending very difficult once the hinge 40 reaches a 90° angle. Because the expandable slots 44*b* comprise elongated slots 54 of insignificant thickness when the hinge is in the neutral position, it is difficult for the hinge to bend in a direction toward the expandable side 48. Accordingly, the depicted hinge 40 is designed to bend in a single plane in a single direction and no more than approximately 90°.

The integrity of the hinge 40 is maintained by including a flexible hinge cover 60 over the hinge. The hinge cover 60 is preferably made of a biocompatible plastic, such as polyurethane, with a flexibility approximately equal to that of the intermediate shaft 14. The hinge cover 60, like the intermediate shaft 14, should not limit the ability of the hinge 40 to bend. The hinge cover 60 protects the hinge 40 against electrical conductivity, particularly when the hinge is made of Nitinol or another metal, and also protects against blood and other bodily fluids from entering and clogging the slots 44 of the hinge. The hinge cover 60 is longer than the hinge 40 and has proximal and distal ends extending beyond the hinge's proximal and distal ends, respectively. The hinge cover 60 can be secured in place over the hinge 40 by any suitable method, such as by gluing or thermally bonding the proximal end of the hinge cover 60 to the distal region 22 of the catheter shaft 12 and by gluing or thermally bonding the distal end of the hinge cover to the distal shaft 16.

Although the hinge 40 is described as being mounted over the intermediate shaft 14, it could also be mounted within the intermediate shaft, for example, if the intermediate shaft has a single central lumen. Other arrangements for the hinge are also within the scope of the invention. For example, the hinge can be formed by providing slots directly into a portion of the tubing that forms the catheter shaft As noted above, the distal shaft 16 carries one or more electrodes for mapping and/or treatment or other treatment or diagnosis devices. In the depicted embodiment, the distal shaft 16 carries a porous electrode arrangement comprising a coil electrode 62 wrapped around a portion of the distal shaft over which is mounted a plastic sleeve 64.

The coil electrode 62 can be made of any electrically-conductive material, such as platinum or gold. The length of the coil electrode 62 can vary depending on the desired application, and preferably ranges from about 5 mm to about 20 mm, more preferably about 11 mm.

The porous sleeve 64 can be made of any suitable biocompatible porous material through which fluid can pass, such as porous polytetrafluoroethylene. Preferably the porous sleeve 64 is sufficiently porous to permit saline to pass therethrough at a flowrate of at least 1 cc/min, more preferably from about 10 cc/min to about 60 cc/min, still more preferably from about 20 cc/min to about 40 cc/min.

One or more irrigation openings 66 are provided in the wall of the distal shaft 16 that fluidly connect the third lumen 34*c* of the distal shaft to the outside of the distal shaft. In the depicted embodiment, the distal shaft 16 includes three irrigation openings 66, although this number can vary as desired. The irrigation openings 66 are provided between the coils of the coiled electrode 62 and underneath the porous sleeve 64. The irrigation openings 66 permit fluid to pass from the third lumen 34*c* of the distal shaft to the outside of the distal shaft within the porous sleeve 64 and then through the porous sleeve. The fluid is preferably saline or other conductive fluid so that current can pass from the coiled electrode 62 and through the fluid so that the fluid can be used to ablate tissue. The proximal and distal ends of the porous sleeve 64 can be attached to the distal shaft 16 by any suitable method that provides a fluid-tight seal to prevent fluid from leaking out the ends of the porous sleeve. In one embodiment, a plastic thread (not shown), such as a Dacron® thread, is wrapped and cinched around the ends of the porous sleeve 64 and then sealed with polyurethane glue or the like. Such a porous electrode arrangement is described in more detail in U.S. patent application Ser. No. 09/073,907, entitled "Irrigated Ablation Device Assembly," the entire disclosure of which is incorporated herein by reference.

To introduce saline or other fluid to the irrigation openings 66, an infusion tube 68 is provided within the catheter shaft 12. The infusion fluid 68 has a distal end mounted in the proximal end of the third lumen 34a in the distal region 22 of the catheter shaft 12, and a proximal end that extends outside the catheter through the control handle 18, but could alternatively extend out through a sidearm, as is generally known in the art. A luer hub 69 is mounted on the proximal end of the infusion tube 68 so that fluid can be introduced into the infusion tube, through the third lumen 34a in the distal region 22 of the catheter shaft 12, through the third lumen 34b of the intermediate shaft 14, through the third lumen 34c of the distal shaft 16 and out through the irrigation openings 66. In the depicted embodiment, the distal end of the distal shaft 16 is sealed with polyurethane glue or the like to prevent fluid from passing out through the distal end of the third lumen 34c, although other mechanisms for closing the distal end of the distal shaft can also be used.

Additionally, an electrode lead wire 70 is provided to electrically connect the coil electrode 62 to a source of radio frequency (RF) energy or other type of ablation energy. The electrode lead wire 70 extends through the central lumen 24 of the proximal region 20 of the catheter shaft 12, through the first lumen 30a of the distal region 22 of the catheter shaft, through the first lumen 30b of the intermediate shaft 14, through the first lumen 30c of the distal shaft 16, and out through a lead wire opening (not shown) in the distal shaft. Within the central lumen 24 of the catheter shaft 12, the lead wire 70 extends through a protective tube 71 to prevent the lead wire from interfering with other components in the central lumen, although the protective tube can be eliminated if desired. Preferably the lead wire opening is potted with polyurethane glue or the like to prevent fluid from passing into the first lumen 30c through the lead wire opening. The distal end of the lead wire 70 is then soldered, welded or otherwise electrically connected to the underside of the coil electrode 62. The proximal end of the lead wire 70 extends through the control handle 18 and is connected to a suitable connector (not shown), which can be part of the control handle, that is connected to a source of ablation energy, as is generally known in the art.

In the depicted embodiment, the distal shaft 16 also carries four ring electrodes 72, although the presence and number of the ring electrodes can vary as desired. The ring electrodes 72 are particularly useful for mapping electrical activity within the heart and can be electrically connected to an appropriate monitoring apparatus (not shown) as is generally known in the art. Two ring electrodes 72 are mounted distal to the coil electrode 62, and the other two are mounted proximal to the coil electrode, all within the porous sheath 64. Alternatively, the ring electrodes 72 can be mounted over the proximal and distal ends of porous sheath 64 so long as they do not extend over the region over which the coil electrode 62 extends. Lead wires 70 electrically connect the ring electrodes 72 to a monitoring apparatus in a manner similar to the connection of a lead wire to the coil electrode or in any other manner known to those skilled in the art.

One or more thermocouples 74 can also be provided for monitoring the temperature of the tissue being ablated. In the depicted embodiment, two thermocouples 74 are provided, one just proximal to the coiled electrode 62 and one just distal to the coiled electrode. In addition or in the alternative, thermocouples could be provided in other locations, such as between the coils of the coiled electrode, or eliminated altogether. Each thermocouple comprises a pair of thermocouple wires 74 that extend, along with the lead wires 70, through the central lumen 24 of the proximal region 20 of the catheter shaft 12, through the first lumen 30a of the distal region 22 of the catheter shaft, through the first lumen 30b of the intermediate shaft 14, through the first lumen 30c of the distal shaft 16 and out through a thermocouple opening (not shown) in the distal shaft. The thermocouple openings are preferably potted with polyurethane glue or the like to hold the thermocouples 74 in place and to prevent fluid from passing into the first lumen 30c of the distal shaft 16.

As would be recognized by one skilled in the art, the distal shaft 16 can carry a variety of other electrode configurations. Other particularly useful electrode configurations for use with the inventive hinge design are described in U.S. Pat. No. 6,371,955, U.S. patent application Ser. No. 09/551,467, entitled "Catheter Having Mapping Assembly," U.S. patent application Ser. No. 10/107,899, entitled "Bidirectional Catheter Having Mapping Assembly," and U.S. patent application Ser. No. 10/118,680, entitled "Catheter Having Circular Ablation Assembly," the entire disclosures of which are incorporated herein by reference. The distal shaft 16 could also carry other measurement and/or treatment devices, such as optic fibers, needles or balloons. The particular measurement or treatment device carried by the catheter is not critical to the invention.

The catheter can also include a mechanism for deflecting the distal region 22 of the catheter shaft 12. In the depicted embodiment, a puller wire 76 extends through proximal region 20 of the catheter shaft 12, is anchored at its proximal end to the control handle 18, and is anchored at its distal end to the distal region 22 of the catheter shaft. The puller wire 76 is made of any suitable metal, such as stainless steel or Nitinol, and is preferably coated with Teflon® or the like. The coating reduces the surface friction on the puller wire 76 during deflection.

A compression coil 78 is situated within the proximal region 20 of the catheter shaft 12 in surrounding relation to the puller wire 76. The compression coil 78 extends from the proximal end of the catheter shaft 12 to the proximal end of the distal region 22 of the catheter shaft. The compression coil 78 is made of any suitable metal, preferably stainless steel. The compression coil 78 is tightly wound on itself to provide flexibility, i.e., bending, but to resist compression. The inner diameter of the compression coil 78 is preferably slightly larger than the diameter of the puller wire 76. The Teflon® coating on the puller wire 76 allows it to slide freely within the compression coil 78. If desired, the outer surface of the compression coil 78 is covered by a flexible, non-conductive sheath 80, e.g., made of polyimide tubing, to prevent contact between the compression coil and the lead wires and/or thermocouple wires within the catheter shaft 12.

The compression coil 78 is anchored at its proximal end to the outer wall 26 of the catheter shaft 12 by proximal glue joint 82 and at its distal end to the distal region 22 by distal glue joint 84. Both glue joints 82 and 84 preferably comprise polyurethane glue or the like. The glue may be applied by means of a syringe or the like through a hole made between the outer surface of the catheter shaft 12 and the central lumen 24.

Figure 11:
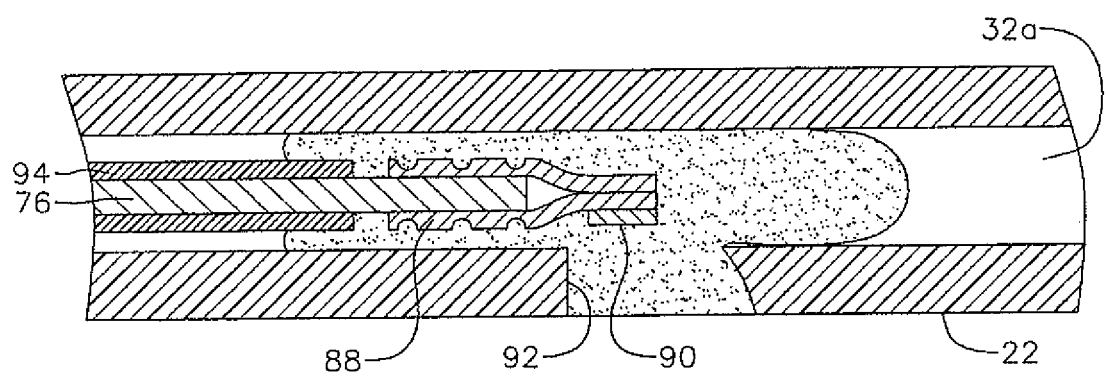
FIG. 11 is a cross sectional view of a portion of the catheter tip section showing one means for attaching the puller wire.
Figure 12:
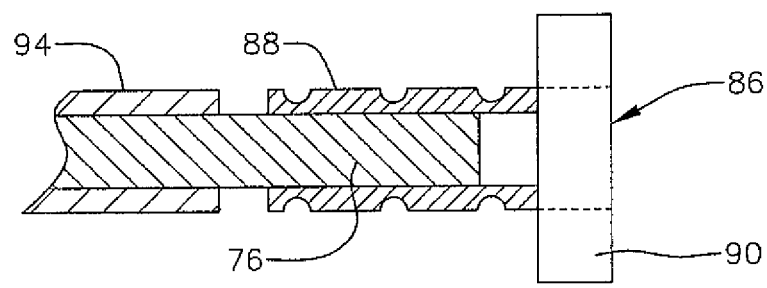
FIG. 12 is a top cross sectional views of a preferred puller wire anchor.
Figure 13:
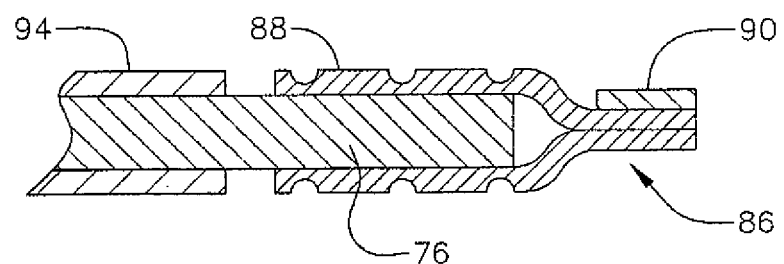
FIG. 13 is a side cross sectional views of the puller wire anchor of FIG. 12.

The puller wire 76 extends into the second lumen 32a of the distal region 22 of the catheter shaft 12. Preferably the puller wire 76 is anchored at its distal end to the side of the distal region 22, as shown in FIGS. 11 to 13. A T-shaped anchor 86 is formed which comprises a short piece of tubular stainless steel 88, e.g., hypodermic stock, which is fitted over the distal end of the puller wire 76 and crimped to fixedly secure it to the puller wire. The distal end of the tubular stainless steel 88 is fixedly attached, e.g., by welding, to a stainless steel cross-piece 90, such as stainless steel ribbon or the like. The cross-piece 90 sits in a notch 92 in a wall of the distal region 22 that extends into the second lumen 32a. The stainless steel cross-piece 90 is larger than the notch 92 and, therefore, cannot be pulled through the notch. The portion of the notch 92 not filled by the cross-piece 90 is filled with glue or the like, preferably a polyurethane glue, which is harder than the material of the distal region 22. Rough edges, if any, of the cross-piece 90 are polished to provide a smooth, continuous surface with the outer surface of the distal region 22. Within the second lumen 32a of the distal region 22, the puller wire 76 extends through a plastic, preferably Teflon®, puller wire sheath 94, which prevents the puller wire 76 from cutting into the wall of the distal region 22 when the distal region is deflected. Any other suitable technique for anchoring the puller wire 76 in the distal region 22 can also be used. Alternatively, other means for deflecting the distal region can be provided, such as the deflection mechanism described in U.S. Pat. No. 5,537,686, the disclosure of which is incorporated herein by reference.

Longitudinal movement of the puller wire 76 relative to the proximal region 20 of the catheter shaft 12, which results in deflection of the distal region 22, is accomplished by suitable manipulation of the control handle 18. Examples of suitable control handles for use in the present invention are disclosed, for example, in U.S. Pat. Nos. Re 34,502 and 5,897,529, the entire disclosures of which are incorporated herein by reference. However, the precise structure of the control handle is not critical so long as it is capable of manipulating the puller wire or other means for deflecting the distal region.

If desired, two or more puller wires can be provided to enhance the ability to manipulate the tip section. In such an embodiment, a second puller wire and a surrounding second compression coil extend through the catheter body and into an additional off-axis lumen in the tip section. The first puller wire is preferably anchored proximal to the anchor location of the second puller wire. Suitable designs of catheters having two or more puller wires, including suitable control handles for such embodiments, are described, for example, in U.S. Pat. Nos. 6,171,277, 6,123,699, 6,183,463, and 6,198,974, the disclosures of which are incorporated herein by reference.

Because in the depicted embodiment the puller wire 76 terminates in the catheter shaft 12, the second lumens 32b and 32c of the intermediate shaft 14 and the distal shaft 16 are empty. However, if desired, the puller wire 76 could instead be anchored in the distal shaft 16 in manner essentially identical to that described above with respect to the distal region 22 of the catheter shaft 12 so as to permit the use to actively deflect the distal shaft. Alternatively, separate puller wires (not shown) could be provided for deflection of the distal region 22 of the catheter shaft 12 and for deflection of the distal shaft 16.

In use, a suitable guiding sheath is inserted into the patient. An example of a suitable guiding sheath for use in connection with the present invention is the Preface™ Braided Guiding Sheath, commercially available from Biosense Webster (Diamond Bar, Calif.). The distal end of the sheath is guided into one of the atria or other region of the heart. A catheter according to the present invention is fed through the guiding sheath until its distal end extends out of the distal end of the guiding sheath.

Once inside the heart, the distal shaft is positioned for the desired mapping or treatment procedure. If the distal shaft carries a porous electrode, the porous electrode can then be used to form continuous linear lesions by ablation. If the distal shaft carries other electrode arrangements, the electrodes can be used for ablating or mapping, as desired. If the distal shaft carries some other component, such as a balloon or optic fiber, that other component can be used for diagnosis and/or treatment as is generally known in the art. The positioning of the distal shaft can be performed by simply pushing the distal shaft against the heart tissue to thereby cause the distal shaft to deflect or bend toward the catheter shaft. The presence of the hinge will enhance the ability of the distal shaft to bend in a single plane in the desired direction and can also limit the extent to which the distal shaft bends. Alternatively, if a puller wire or other deflection mechanism is provided within the distal shaft, the user can actively deflect or bend the distal shaft, with the hinge again serving to enhance the ability of the distal shaft to bend in a single plane in the desired direction and optionally limit the extent to which the distal shaft bends.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:
1. A catheter comprising:
a catheter shaft including a proximal region having a first flexibility, and a distal region having a second flexibility different from the first flexibility;
an intermediate shaft at a distal end of the distal region of the catheter shaft, the intermediate shaft having a longitudinal axis and a third flexibility that is different from both the first flexibility of the proximal region of the catheter shaft and the second flexibility of the distal region of the catheter shaft, the intermediate shaft having a hinge region comprising an expandable side and a compressible side opposite the expandable side, the hinge region further comprising at least one first slot on the expandable side and at least one second slot on the compressible side, the at least one first slot and the at least one second slot being generally transverse to the longitudinal axis of the intermediate shaft, the at least one first slot having a first thickness and the at least one second slot having a second thickness, the first and second thicknesses being different from each other when the hinge region is in a straight position, the hinge region being configured to reversibly bend from the straight position in only a single direction as defined by the at least one first slot and the at least one second slot and configured to prohibit bending from the straight position in a direction opposite the single direction; and a distal shaft at a distal end of the intermediate shaft, the distal shaft having a fourth flexibility that is different from at least the third flexibility of the intermediate shaft.

2. The catheter according to claim 1, further comprising:
a control handle at a proximal end of the catheter shaft; and
a puller wire having a distal end anchored in the intermediate shaft and a proximal end anchored in the control handle, wherein longitudinal movement of the puller wire results in deflection of the intermediate shaft.

3. The catheter according to claim 1, wherein the at least one first slot and the at least one second slot together comprise 10 to 30 slots.

4. The catheter according to claim 1, wherein the at least one first slot comprises 7 slots, and the at least one second slot comprises 7 slots.

5. The catheter according to claim 1, wherein the at least one first slot includes a plurality of first slots or the at least one second slot includes a plurality of second slots, each of the plurality of first slots or the plurality of second slots having a depth such that the slot does not pass through the longitudinal axis of the intermediate shaft.

6. The catheter according to claim 5, wherein the plurality of first slots and the plurality of second slots are aligned such that corresponding first and second slots are positioned a same distance from an end of the intermediate shaft.

7. The catheter according to claim 1, wherein the at least one first slot and/or the at least one second slot includes a plurality of slots of equal depth.

8. The catheter according to claim 1, wherein the at least one first slot and/or the at least one second slot includes a plurality of slots of varying depths.

9. The catheter according to claim 1, wherein the at least one first slot has a first depth, and the at least one second slot has a second depth that is different from the first depth of the at least one first slot.

10. The catheter according to claim 1, wherein the at least one first slot and the at least one second slot have equal depths.

11. The catheter according to claim 1, wherein the third flexibility of the intermediate shaft is greater than the first flexibility of the proximal region of the catheter shaft and the second flexibility of the distal region of the catheter shaft.

12. The catheter according to claim 1, wherein the third flexibility of the intermediate shaft is greater than the fourth flexibility of the distal shaft.

13. The catheter according to claim 1, wherein:
the proximal region of the catheter shaft comprises a 72D durometer material;
the distal region of the catheter shaft comprises a 55D durometer material;
the intermediate region comprises a 35D durometer material; and
the distal shaft comprises a 72D durometer material.

14. The catheter according to claim 1, wherein the distal shaft carries one or more electrodes, diagnostic devices or treatment devices.

15. The catheter according to claim 1, wherein the distal shaft carries one or more mapping electrodes.

16. The catheter according to claim 1, wherein the hinge region covers the entire intermediate shaft.

17. The catheter according to claim 1, wherein the at least one first slot comprises a plurality of first slots and the at least one second slot comprises a plurality of second slots, each of the plurality of first slots having a depth such that the slot passes through the longitudinal axis of the intermediate shaft, and the plurality of first slots and the plurality of second slots being offset in position.

18. The catheter according to claim 1, further comprising a flexible hinge cover over the hinge region of the intermediate shaft.

19. The catheter according to claim 17, wherein the flexible hinge cover comprises polyurethane.

20. The catheter according to claim 17, wherein the hinge cover has a length longer than a length of the hinge region.

* * * * *